(12) United States Patent
Polo (10) Patent No.: US 9,603,585 B2
(45) Date of Patent: Mar. 28, 2017

(54) CORE BIOPSY SCISSORS

(71) Applicant: Oscar R Polo, Portland, OR (US)

(72) Inventor: Oscar R Polo, Portland, OR (US)

( * ) Notice: Subject to any disclaimer, the term of this patent is extended or adjusted under 35 U.S.C. 154(b) by 685 days.

(21) Appl. No.: 13/681,447

(22) Filed: Nov. 20, 2012

(65) Prior Publication Data

US 2014/0142602 A1    May 22, 2014

(51) Int. Cl.
*A61B 17/32*    (2006.01)
*A61B 10/02*    (2006.01)

(52) U.S. Cl.
CPC .................................. *A61B 10/02* (2013.01)

(58) Field of Classification Search
CPC .............. A61B 17/32002; A61B 17/32; A61B 17/32053; A61B 17/320016; A61B 2017/32; A61B 2017/32004; A61B 2017/320016; A61B 2017/00349; A61B 2017/2939; A61B 2017/320064; A61B 2017/2944; A61B 2017/00353; A61B 2017/00685; A61B 2010/0208; A61B 10/0275; A61B 10/02; A61B 10/06; A61B 10/0266; A61B 10/04
USPC ......................................................... 606/174
See application file for complete search history.

(56) References Cited

U.S. PATENT DOCUMENTS

| | | | | |
|---|---|---|---|---|
| 4,682,606 A | * | 7/1987 | DeCaprio | ...................... 600/567 |
| 4,881,550 A | * | 11/1989 | Kothe | ..................... A61B 10/02 600/564 |
| 5,074,311 A | * | 12/1991 | Hasson | ......................... 600/567 |
| 5,391,166 A | * | 2/1995 | Eggers | ............... A61B 18/1206 606/170 |
| 5,715,832 A | * | 2/1998 | Koblish | ............. A61B 18/1445 600/564 |
| 5,871,453 A | * | 2/1999 | Banik | ................ A61B 10/0266 600/564 |
| 6,142,957 A | * | 11/2000 | Diamond | ............ A61B 10/0266 600/567 |
| 7,258,694 B1 | * | 8/2007 | Choi | ................ A61B 17/32053 606/174 |
| 2003/0158498 A1 | * | 8/2003 | Bakry | .................... A61B 10/04 600/562 |
| 2010/0280407 A1 | * | 11/2010 | Polster | ......................... 600/566 |
| 2012/0143218 A1 | * | 6/2012 | Beardsley et al. | ............ 606/142 |

* cited by examiner

*Primary Examiner* — Katherine M Shi
*Assistant Examiner* — Mohamed Gabr
(74) *Attorney, Agent, or Firm* — Baumgartner Patent Law; Marc Baumgartner (57) ABSTRACT

Core biopsy scissors capable of one-handed use by a medical professional, and include blades capable of making a rotatable core cut, in addition to elevating, clipping, and collecting a sample from targeted tissue in a patient.

10 Claims, 8 Drawing Sheets

CORE BIOPSY SCISSORS

FIELD OF THE INVENTION

The embodiments herein relate to the field of medicine, and more particularly to core biopsy scissors for use in collecting a tissue sample from a patient.

BACKGROUND

A biopsy is a medical test commonly performed by a medical professional that involves the collection of tissue from a patient for closer examination to detect abnormalities, such as precancerous and cancerous cells. One type of common biopsy is a punch biopsy that collects a core of tissue from a patient. Currently this procedure generally involves a plurality of different medical instruments. More specifically, a handled circular blade is positioned at the location where the tissue sample is to be taken. The medical professional then applies pressure to the handle and manually rotates the handle to rotate the blade into the tissue sample. After the circular cut is made, the blade is removed and discarded. The medical professional then uses forceps in one hand to raise the anchored sample out of its cylindrical cavity. With the other hand the provider uses scissors to snip the elevated tissue at its tethered base to excise the sample. This process requires the doctor to use both hands and three instruments: blade, forceps, and scissors. Accordingly there is a need in the art to simplify this process, such that a doctor can utilize one instrument in one hand to collect the targeted tissue sample.

Prior art attempts to design a one handed biopsy cutting and collection device fail to address the problems solved by the embodiments disclosed herein. As one example, U.S. Patent Publication No. 2006/0178,699 "Biopsy Forceps" to Surti teaches forceps designed to grasp or tear at a sample as opposed to circularly cutting around and into the sample utilizing a rotational mechanism. The forceps taught by Surti was not designed to singlehandedly perform a barrel cut around the tissue sample and to snip the base of the sample. The device taught by Surti can lead to jagged edges and may compromise the histological integrity of the sample site. Utilizing a device operated by a single hand and capable of a core cut, and then elevating and snipping the sample is highly advantageous as it minimizes the use of operating assistants and allows the user to use his free hand for blotting the blood or retracting the tissue for better visualization. Accordingly, there is a need in the art to provide a single biopsy device, operable by one hand that can perform a barrel cut, raise and snip the base of a tissue sample, and collect the sample, while preserving the histological integrity of the target site.

SUMMARY OF THE INVENTION

Preferred embodiments are directed to biopsy scissors comprising a main shaft having an internal channel traversing proximally and distally; an inner shaft traversing proximally and distally within the internal channel of the main shaft; first and second blades configured to close towards each other at first and second hinge points, operably coupled to and positioned distally from the inner shaft, wherein the first and second blades each have a sharp distal facing edge shaped to collectively make a singular circular cut into a targeted site when axially rotated and travelling distally; a gear transmission configured to rotate the inner shaft and attached blades; and means for moving the inner shaft in proximal and distal directions, wherein proximal movement of the inner shaft is independent of the main shaft, and effectuates the first and second blades to close towards each other and move proximally.

Additional embodiments are directed to a method of collecting a tissue sample from a subject comprising: providing biopsy scissors comprising a main shaft having an internal channel traversing proximally and distally; an inner shaft traversing proximally and distally within the internal channel of the main shaft; first and second blades configured to close towards each other at first and second hinge points, operably coupled to and positioned distally from the inner shaft, wherein the first and second blades each have a sharp distal facing edge shaped to collectively make a singular circular cut into a targeted site when axially rotated and travelling distally; a gear transmission configured to rotate the inner shaft and attached blades; and means for moving the inner shaft in proximal and distal directions, wherein proximal movement of the inner shaft is independent of the main shaft, and effectuates the first and second blades to close towards each other and move proximally; using said biopsy scissors to make a rotational circular cut into the targeted site of the subject and then utilizing means for moving the internal shaft proximally to close the first and second blades towards each other to excise the tissue sample from the subject. Methods of collecting tissue samples provided herein can be used with all disclosed embodiments of scissors.

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE ILLUSTRATED EMBODIMENTS

Embodiments of the present invention are described below. It is, however, expressly noted that the present invention is not limited to these embodiments, but rather the intention is that modifications that are apparent to the person skilled in the art and equivalents thereof are also included.

Figure 1:
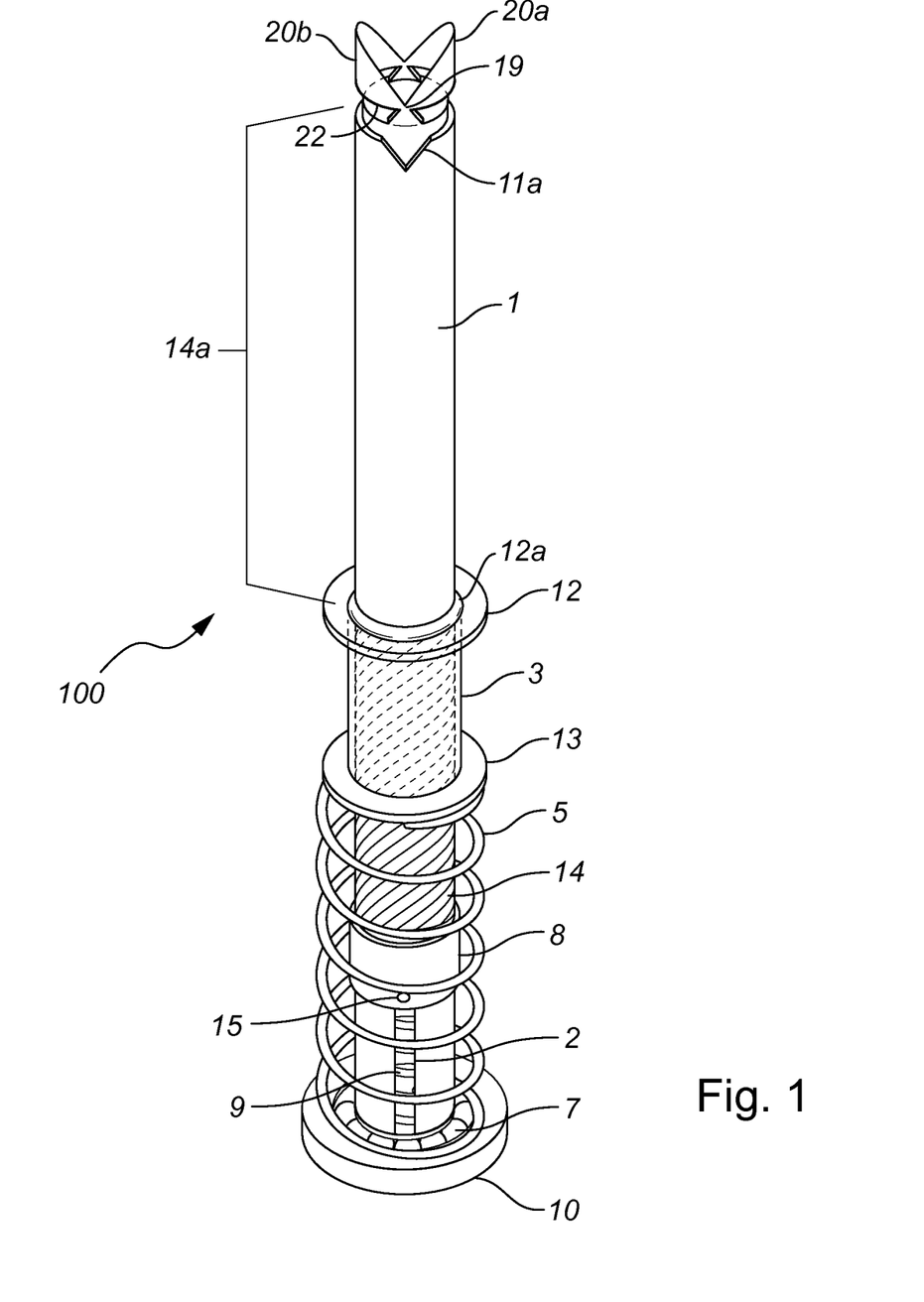
FIG. 1 is a perspective view of assembled core biopsy scissors.

FIGS. 1-4 depict a preferred embodiment of core biopsy scissors 100 having a main shaft 1 with blades 20a and 20b positioned at a distal end and a thumb press 10 positioned at the proximal end. Preferably, the external surface of the main shaft 1 includes a threaded section 14. The entire main shaft can be threaded, but it is preferred that the threaded section 14 is positioned between distal 14a and proximal 14b smooth sections, or otherwise unthreaded sections. Preferably, the threaded portion 14 of the main shaft 1 is an external axial spiral thread, wherein a portion of or the entire threaded section 14 traverses through an aperture of a winged transmission 3 when the scissors 100 are in their natural, uncompressed state. While the threaded section 14 is shown in FIG. 1 as extending a length approximately from the distal end of the outer shaft 8 to the finger rest 12, the threaded section could also be shorter, such as extending at least the approximate length of the winged transmission 3. Still more specifically it is preferred that the winged transmission 3 includes internal spiral threads 16 that are complementary to the external threads 14 of the main shaft 1. The winged transmission 3 can include a finger rest 12 at its distal end and a proximal lip 13 at its proximal end. This configuration allows for a user, such as a medical professional, to hold and operate the scissors 100 like a syringe with one hand. More specifically, the user's thumb is positioned on the proximal face of the thumb rest 10 while their index and middle fingers of the same hand are positioned on the finger rest 12 straddling the main shaft 1. A user can compress the scissors 100 by squeezing his index and middle fingers and thumb towards each other, thereby compressing the thumb press 10 towards the winged transmission 3 and distally pushing the main shaft 1 through the winged transmission 3.

Figures 8, 9:
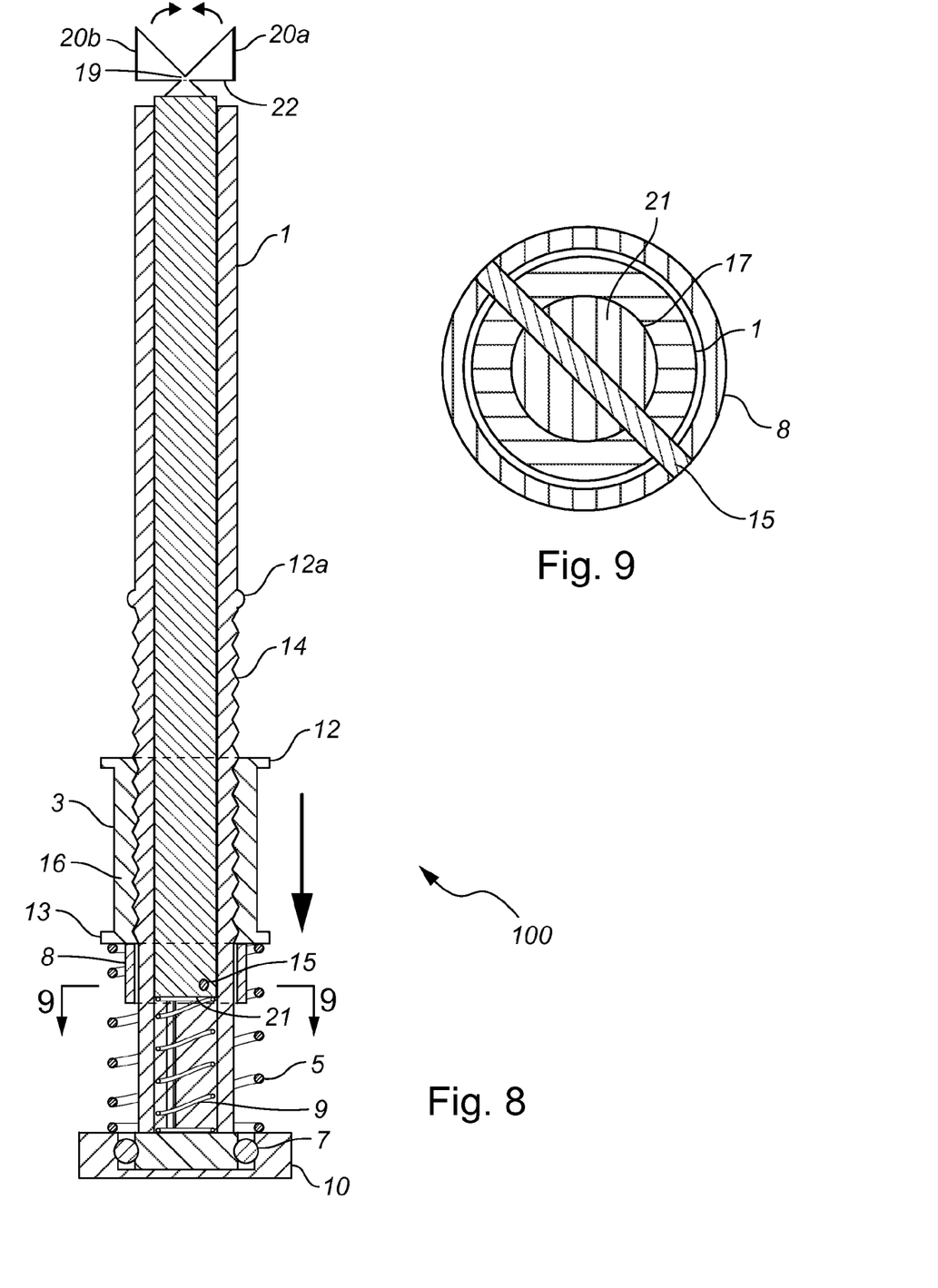
FIG. 8 is a cross-sectional view of core biopsy scissors in a partially compressed state.
FIG. 9 is a cross-sectional view of the outer shaft section of the scissors in a partially compressed state.
Figures 10, 11:
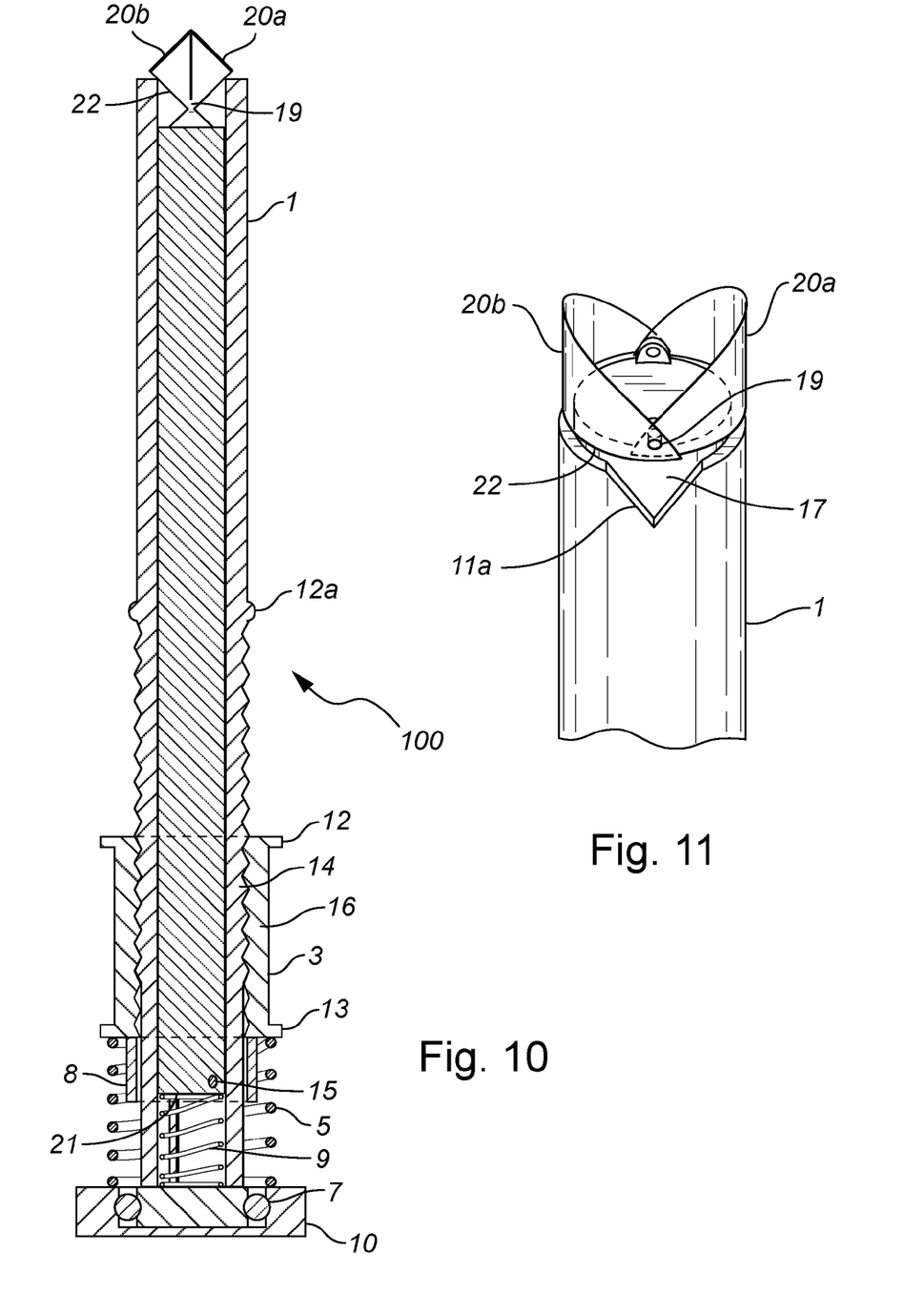
FIG. 10 is a cross-sectional view of core biopsy scissors in a fully compressed state.
FIG. 11 is a perspective view of a first alternative set of blades.

The scissors 100 are shown in a partially compressed state in FIG. 8 and a fully compressed state in FIG. 10. As will be described in more detail below, compressing the thumb press 10 towards the winged transmission 3 causes the distal blades 20a and 20b to first axially rotate forward (away from the winged transmission 3) to create a barrel cut in the targeted tissue and then to close, thereby allowing a user to snip and excise a biopsy sample from a targeted site on the patient.

The proximal face of the proximal lip 13 of the winged transmission 3 preferably abuts against the distal face of the means for elastic compression, such as an external spring 5 that spirals around the main shaft 1 and can be coupled or not to said spring 5. The proximal end of the means for compression, such as the external spring 5, preferably abuts against the thumb press 10, and can be coupled or not to said thumb press 10. The means for compression, or external spring 5, allows for the winged transmission 3 to return to its natural position in an uncompressed state (as shown in FIG. 1) after the user desists in compressing the winged transmission 3 towards the thumb press 10. The fully compressed configuration of the scissors is shown in FIG. 10. The scissors 100 can also include a housing around the outside of the external spring 5 if desired.

Preferably, the main shaft 1 can also include a rim 12a or stop positioned distal to the winged transmission 3 that prevents the winged transmission 3 from travelling farther distally onto the distal external shaft 14a when returning to its uncompressed position. The rim 12a or stop thus would abut against the distal face of the finger rest 12 when the scissors 100 are in their natural, uncompressed configuration, as shown in FIG. 1.

Any suitable means for axial rotation can be used with the main shaft 1 to cause the distal blades 20a and 20b to make a circular cut around the targeted site. According to a preferred embodiment, the threaded section 16 of the winged transmission 3 and the complementary threaded section 14 of the main shaft 1 allows for axial rotation. More specifically, as the main shaft 1 is pushed in a distal direction, through the winged transmission 3, the complementary axially threaded sections 14 and 16 cause the main shaft 1 to rotate forward. This mechanism is similar to the axial rotation of a push drill. Similarly, as the winged transmission 3 returns distally with the assistance of the external spring 5 as compression is released, the main shaft 1 proximally rotates in an opposite direction from its distally moving rotation.

Figures 5, 6, 7:
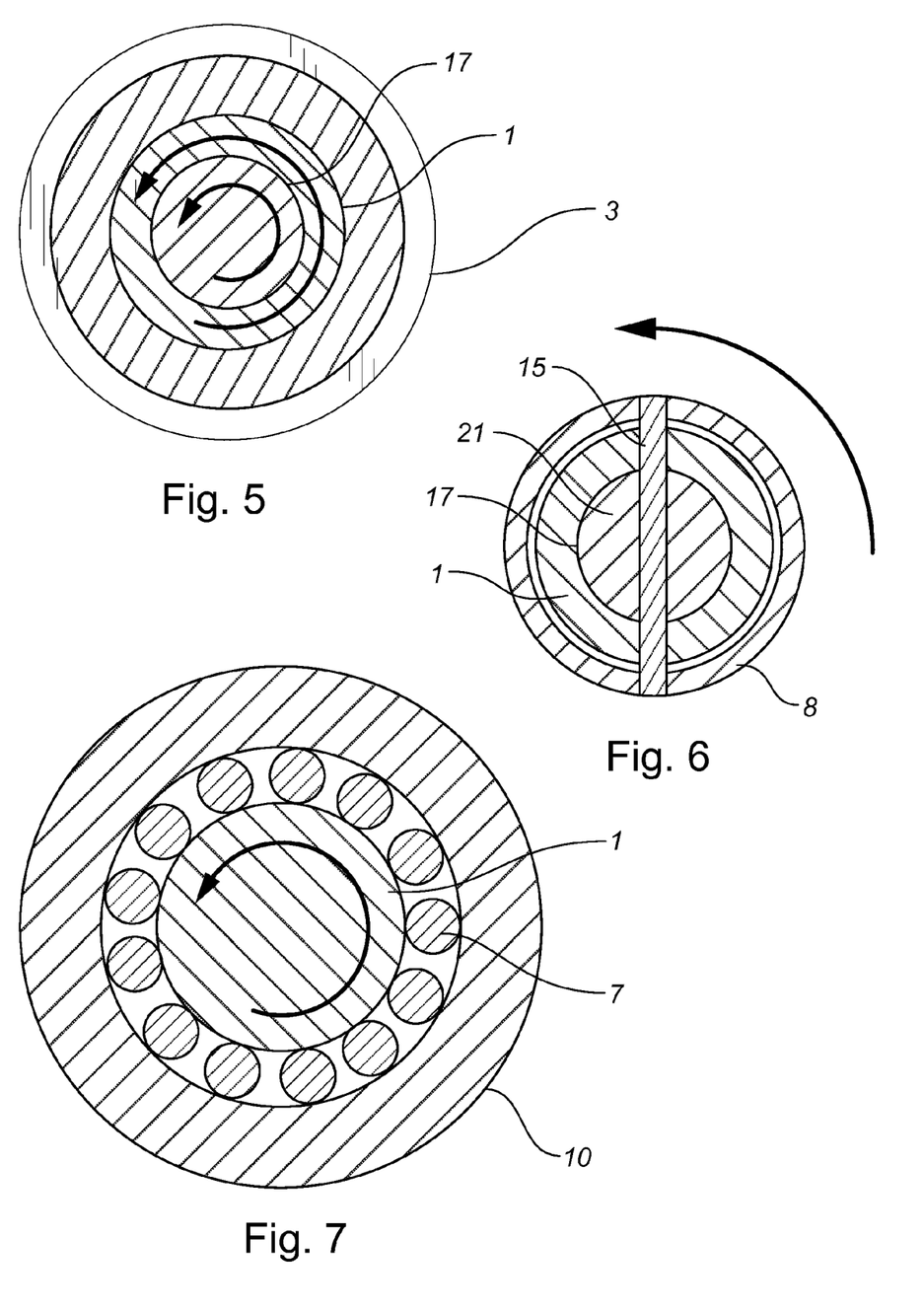
FIG. 5 is a cross-sectional view of the winged transmission section of the scissors.
FIG. 6 is a cross-sectional view of the outer shaft section of the scissors.
FIG. 7 is a cross-sectional view of the thumb press section of the scissors.

As will be described in more detail below, the blades 20a and 20b are operably coupled indirectly to the main shaft 1 such that they rotate in sync and cut a substantially circular perimeter at the targeted site for collection when they are open. To facilitate the axial rotation of the main shaft 1, it is preferred that the proximal end of the main shaft 1 is operably coupled with the thumb press 10 in a way that permits axial rotation. For example, as shown in FIG. 7, the proximal end of the main shaft 1 can be surrounded by ball bearings 7 within the thumb press 10 to facilitate axial rotation and minimize friction. Under this embodiment, the inside of the thumb press 10 functions as a wheel bearing.

The scissors 100 can preferably include an outer shaft 8 positioned on the outside of the main shaft 1 proximal to the winged transmission 3 and within the external spring 5. The shorter outer shaft 8 is preferably operably coupled to an inner shaft 17 positioned within and having a shorter length than that of the main shaft 1. As one non-limiting example, a pin 15 can traverse across the diameter of the outer shaft 8, and through appropriately sized holes 18 within the inner shaft 17. During compression, as the thumb press 10 approaches the winged transmission 3, the proximal lip 13 eventually engages with the distal end of the outer shaft 8 and presses it proximally towards the thumb press 10. As the outer shaft 8 is operably coupled to the inner shaft 17 (e.g., through a pin 15), when the outer shaft 8 moves proximally, it forces the inner shaft 17 to simultaneously move proximally in the same direction. As will be discussed in more detail below, the pulling of the inner shaft 17 in a proximal direction eventually forces the blade members 20a and 20b to close towards each other, such as shown in FIG. 10. The closure of the blades 20a and 20b defines a clipping action, designed to raise and completely excise the biopsy sample from the target site in the patient, and is different from the original rotational incision discussed above that creates a circular cut around the sample. It is important to note that a user can cut a progressively deeper core incision by applying slight pressure into the blades 20a and 20b into the targeted tissue and continuingly compressing the winged transmission 3 towards the thumb press 10 without engaging the outer shaft 8 with the proximal lip 13 of the winged transmission 3. According to this particular use, it is preferred that the blades 20a and 20b and the proximal flange 22 do not have a diameter greater than the main shaft 1.

Figure 4:
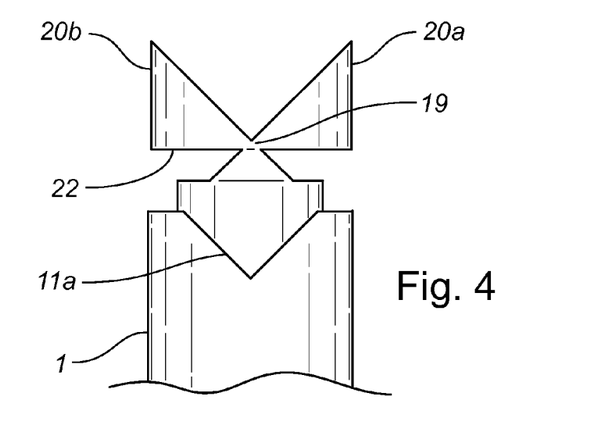
FIG. 4 is a close-up view of the blades and the proximal portion of the scissors.

As shown in detail in FIG. 4, the inner shaft 17 can include a proximal surface 21 that abuts against or is otherwise operably coupled to the distal portion of an internal spring 9, or other resilient means, positioned within the main shaft 1. The internal spring 9 is preferred to be in a partially compressed state when the scissors 100 are in their natural, uncompressed configuration, as shown in FIG. 1. In this partially compressed state, the internal spring 9 pushes the inner shaft 17 in a distal direction and keeps the pin 15 pressed against the distal ends of the slot 2 positioned in the proximal section 14b of the main shaft 1, which are described below. As shown in FIG. 10, the internal spring 9 compresses further as the inner shaft 17 moves proximally towards the thumb press 10. Likewise, the internal spring 9 partially expands after the compression of the winged transmission 3 is released and forces the inner shaft 17 in a distal direction, and reopens the closed blades 20a and 20b.

Figure 2:
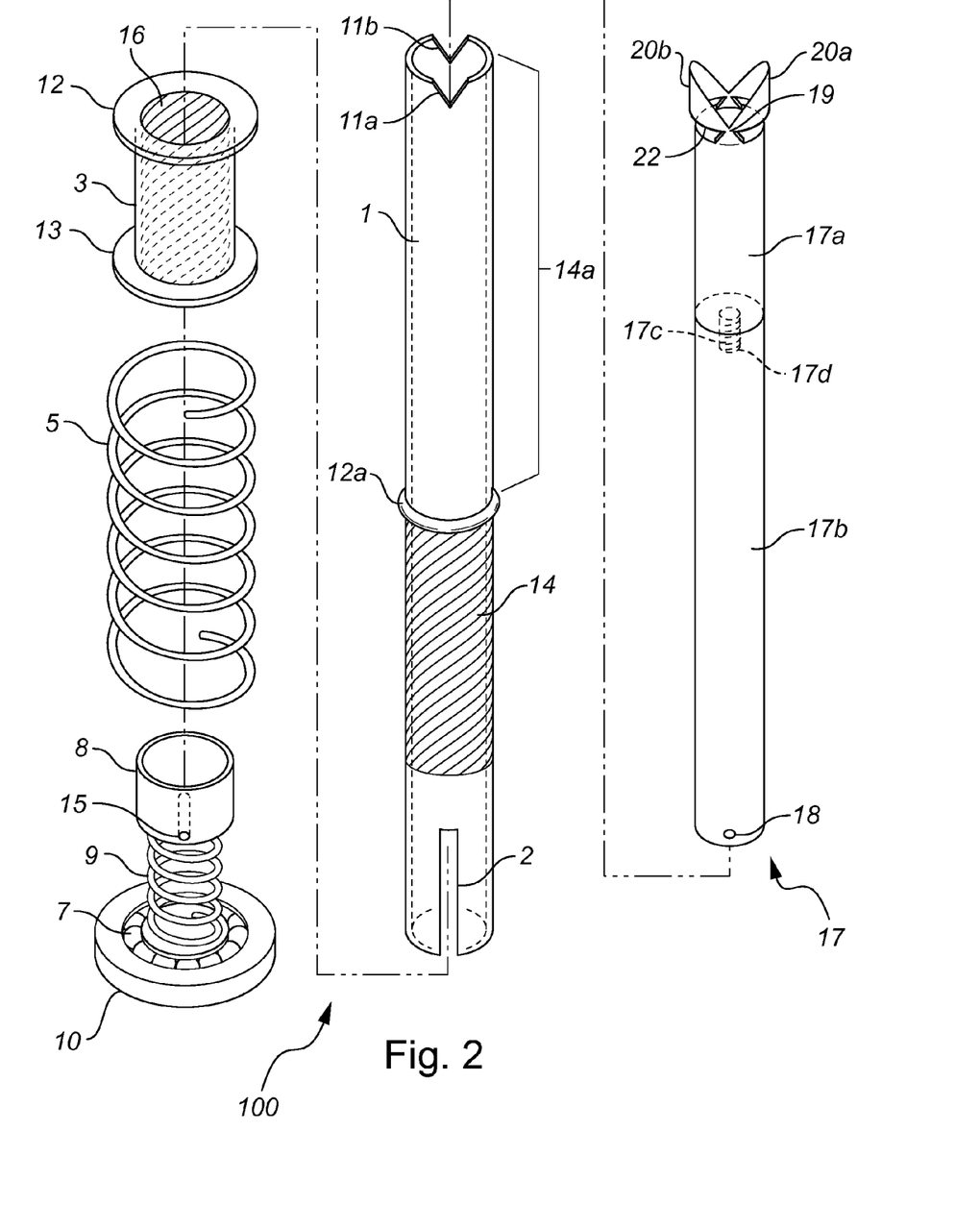
FIG. 2 is a perspective, exploded view of core biopsy scissors.
Figure 3:
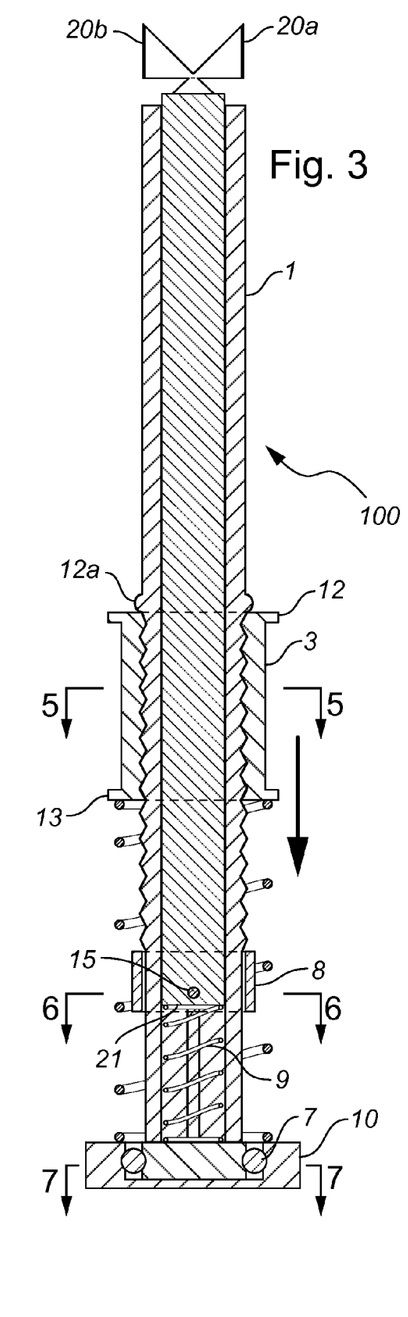
FIG. 3 is a cross-sectional view of core biopsy scissors in an uncompressed state.

According to certain embodiments, the inner shaft 17 can be entirely hollow along its length to act as a receptacle for biopsy samples as they are excised from a patient. However, according to preferred embodiments the inner shaft 17 is partitioned into a disposable distal section 17a that is hollow to act as a receptacle for the biopsy sample and can releasably couple to a proximal section 17b as shown in FIG. 2. As the proximal section 17b is not designed to be a receptacle, it can be hollow, solid, or partially hollow, for example. More specifically, according to this preferred embodiment the distal section 17a can include a male connector 17c that releasably couples to a complementary female connector 17d in the proximal section 17b. The male and female connectors can also be interchanged. As one non-exclusive example, the male connector 17c can be a threaded bolt that can be screwed into the threaded female connector 17b. For embodiments where the male and female connectors 17c and 17d are threaded, it is preferred that they are coupled in a rotating orientation that is opposite than that of the rotation of the blades 20a and 20b when moving in a distal direction. For example, if the blades 20a and 20b rotate clockwise in a distal direction, it is preferred that the male and female threaded connectors 17c and 17d tighten in a counter-clockwise fashion, to prevent inadvertent decoupling of the distal and proximal sections 17a and 17b from each other. Once the biopsy is collected in the inner shaft 17, the distal section 17a can be decoupled from the proximal section 17b, by unscrewing for example. Regardless of whether the inner shaft 17 is entirely or partially hollow, multiple biopsy samples can potentially be collected in the same receptacle before removal. The detachable distal section 17a is also advantageous in allowing a user to select a variety of lengths, shapes, sizes and types of distal sections 17a and/or blades 20a and 20b depending on the location and type of biopsy sample to be collected. The detachable distal section 17a is preferably disposable, but can be configured to be reused after sterilization if desired. According to other embodiments, the entire inner shaft 17 is not hollow.

Another advantageous embodiment of the teachings herein includes two linear slots 2 positioned on opposite sides from each other in the proximal portion 14b of the main shaft 1. As shown in FIGS. 6 and 9, these slots 2 allow the pin 15, or other coupling means, connecting the outer shaft 8 and the inner shaft 17 to pass through the main shaft 1, while the outer shaft 8 (and coupled inner shaft 17) slides in a distal direction towards the blades 20a and 20b or in a proximal direction towards the thumb press 10. When the scissors 100 are in their natural, uncompressed position, as shown in FIG. 1, the pin 15 is pushed against the distal ends of the slots 2 due to the partially compressed internal spring 9. The sides of the slots 2 also preferably abut or narrowly enclose the pin 15. This configuration is advantageous as it causes the inner shaft 17 along with the blades 20a and 20b to axially rotate in both distal and proximal directions in sync with the outer shaft 1, such as shown in FIGS. 5 and 9.

Figure 12:
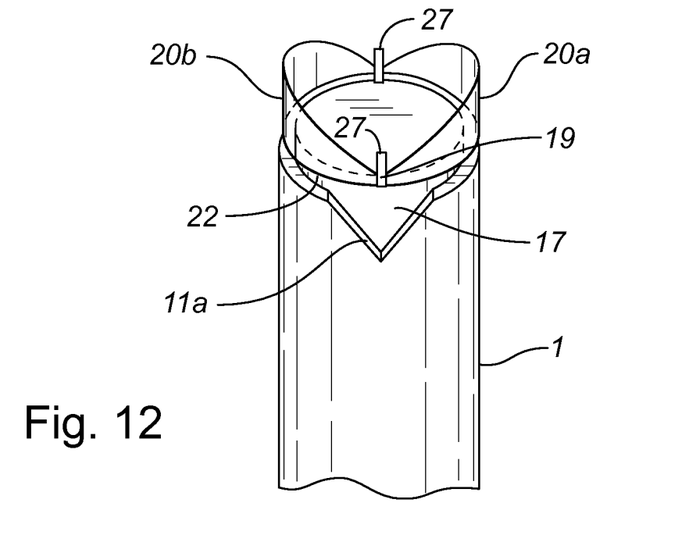
FIG. 12 is a perspective view of a second alternative set of blades.

The distal portion of the inner shaft 17 is coupled to the proximal ends of blades 20a and 20b that are capable of three advantageous functions (1) a rotating circular, barrel cut around the biopsy sample when the blades 20a and 20b are in an open position (see FIG. 1) and (2) a clipping action where the blades 20a and 20b close towards each other (see FIG. 10) and (3) a raising action where the sample is lifted from its tissue source. A variety of blade designs can accomplish these three functions. As described below, FIGS. 1-4, 8 and 10 shows one preferred set of blades 20a and 20b whiles FIGS. 11 and 12 show two non-exclusive variations of blades 20a and 20b.

While any suitable shape of blades can be used for the above functions, it is generally preferred the scissors 100 utilize two, semicircular blades 20a and 20b that are mirror images of each other. The distal portion/edge of the blades 20a and 20b should be sufficiently sharp to allow for the coring, circular cut. When rotating the distal portion/edge of the open blades cut a circular or substantially circular cut around the sample tissue to be collected. The final barrel cut resembles an incision made by punching a sharp tube into the sample site.

The inward edges of the blades may be turned inward (beveled) a few degrees and may have concave inward faces, similar to two scoops facing each other. The blades 20a and 20b can include two pivot or bend points 19, or hinges, positioned at opposite sides from each other that couple the blades 20a and 20b proximal ends to each other, and allow the blades 20a and 20b to open and close. The term "hinge point" can include both bend points and hinges. The main shaft 1 preferably includes two angular notches 11a and 11b positioned 180° from each other around the main shaft 1, and below the hinges or bend points 19 of the blades 20a and 20b. These notches 11a and 11b allow space for the bend points 19 to work in closing and opening the blades 20a and 20b. The diameter of the proximal end of the blades, in the open position, is at least equal to the diameter of the distal end of the main shaft 1. As the inner shaft 17 is forced proximally, toward the thumb rest 10 of the scissors 100, the proximal end of the blades 22 catches on the outside diameter of the distal end of the main shaft 1, thereby bringing the blades 20a and 20b together and sliding them into the angled notches 11a and 11b and hollowed section of the main shaft 1, as shown in FIG. 10. This blade mechanism effectively elevates the tissue sample and clips it base. While shown only partway inside the main shaft 1 in FIG. 10, it is also readily contemplated to configure the shape of the blades 20a and 20b such that they fully retract within the main shaft 1.

When in the closed position (see for example, FIG. 10) the blades 20a and 20b are angled towards each other, preferably between 60 and 90 degrees, and may or may not touch each other. It is preferred that the blades 20a and 20b do touch each other in this position, or substantially so, to help facilitate a clean excision of the sample from the tissue, and to retain the sample within the blades 20a and 20b after excision, as opposed to having the sample falling through a gap between blades 20a and 20b. The collected tissue is thus retained in the blades 20a and 20b and/or the distal portion of the inner shaft 17. According to advantageous embodiments, multiple biopsies can be collected with the main shaft 1 prior to emptying, wherein older samples are pushed proximally within the inner shaft 17 as newer samples are collected. The size and specific shape of the blades 20a and 20b can be selected prior to the cutting so the user can predetermine the size of the collected sample(s). Different sizes and shapes of blades 20a and 20b (and scissors 100) can be selected based on the position and the type of the target tissue.

The blades 20a and 20b shown in FIGS. 1-4, 8 and 10 are cut out from the flanged distal end of the inner shaft 17. According to this embodiment the inner shaft 17 is flanged at its distal end and is of at least the same diameter as the distal end of the main shaft 1. Preferably the inner shaft 17 and blades 20a and 20b are made of an elastic metal or a shape-memory alloy, such as Nickel titanium, also known as nitinol. These materials, provides strength to the blades to 20a and 20b and allow them to close and easily return back to their natural open shape when clipping the sample. Alternatively, a proximal stop 22a can be positioned below the blades 20a and 20b that has a larger diameter than the main shaft 1 and provides a stop for penetrating the tissue any further. The stop 22a can be of the same diameter as the blades 20a and 20b or of a larger diameter than the blades 20a and 20b.

Similar to FIGS. 1-4, 8, and 10 the blades in FIG. 12 are made of an elastic material having the strength to make circular and clipping cuts. More specifically, the blades 20a and 20b are made of an elastic metal or a shape-memory alloy, such as Nickel titanium. These materials, provides strength to the blades to 20a and 20b and allow them to close and easily return back to their natural open shape. Preferably the blades 20a and 20b include a proximal flange 22 having a diameter that is greater than the diameter of the inner shaft 17 and is the same, or substantially so, as the outer shaft 1, more particularly the distal non-threaded section of the shaft 1 above the threaded section 14. The difference between FIG. 12 and FIGS. 1-4, 8, and 10 is that the blades are not necessarily cut out of the inner shaft 17 and can be a separate material. These blades 20a and 20b can be attached to the inner shaft 17 using thin strips 27. More specifically, the inner shaft 17 includes internal strips 27 that extend upward and over the bend point 19 of the blades 20a and 20b and couples to the outer part of the inner shaft 17. This coupling can be done using any suitable means such as soldering or welding, for example.

According to FIG. 11, the blades 20a and 20b are coupled to the inner shaft 17 in a different way. According to this embodiment, the distal end of the inner shaft 17 includes two hinges 19 that couples to the blades 20a and 20b and allows them to open and close, such as through the use of pins and holes. The hinges 19 can further include one or more springs, or other elastic means to facilitate the blades 20a and 20b returning to their natural positions.

Figure 13:
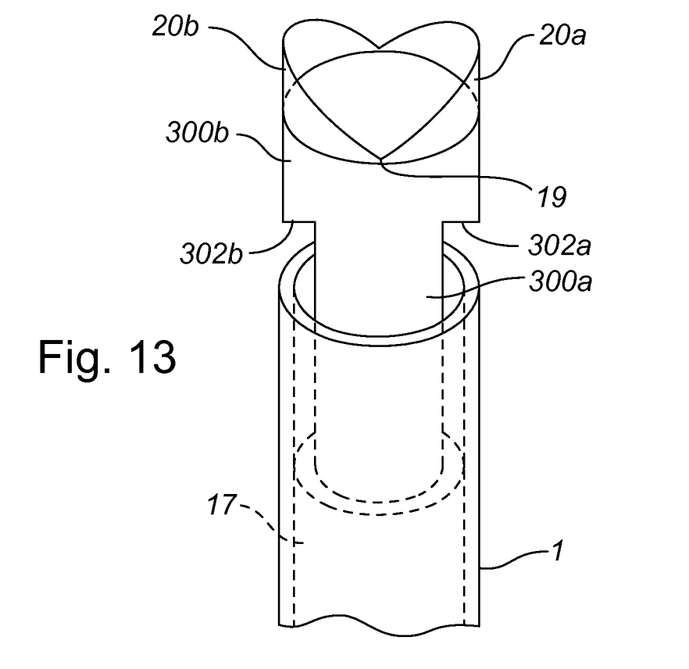
FIG. 13 is a perspective view of a third alternative set of blades in an open position.

According to still another embodiment, the blades 20a and 20b can be closed using two resilient ribbons 300a and 300b as shown in FIG. 13. More specifically, in their natural position, when the blades 20a and 20b are in an open position (FIG. 13), resilient ribbons 300a and 300b connect to the distal section of the inner shaft 17, extend distally to bend points 302a and 302b that extend outward, then extend distally to operably couple to the blades 20a and 20b. The ribbons 300a and 300b can be angulated outwards approximately between 60-90° at the bend points 302a and 302b, when the blades 20a and 20b are in the open position (FIG. 13a). The bend points 302a and 302b are configured to catch on the outer diameter of the distal section 14a of the outer shaft 1 when the inner shaft 17 is pulled in proximally. It is preferred that the external diameter of the inner shaft 17 is less than the diameter of the cutting circular blades 20a and 20b in the open position. When the inner shaft 17 is pulled proximally, the bend points 302a and 302b catch on the distal diameter of the stationary outer shaft 1 which straightens out the ribbons 300a and 300b simultaneously as they are pulled into the outer shaft 1. This motion rotates the blades 20a and 20b inward and pulls them proximal. This results in the distal end of the blades 20a and 20b coming in contact with each other, or substantially so in the closed position. Preferably, in the open position, the ribbons 300a and 300b and the sharp edges of both blades 20a and 20b are facing distally, parallel to the axis of the main shaft 1, or substantially so. In this position the blades 20a and 20b can define the perimeter of a circle, or substantially so. According to an alternative embodiment, not shown, the thumb rest and finger rest can extend in one direction (inferiorly) such that the extended thumb rest acts as a palm rest and the extended finger rest acts as a finger grip.

Figures 14, 15:
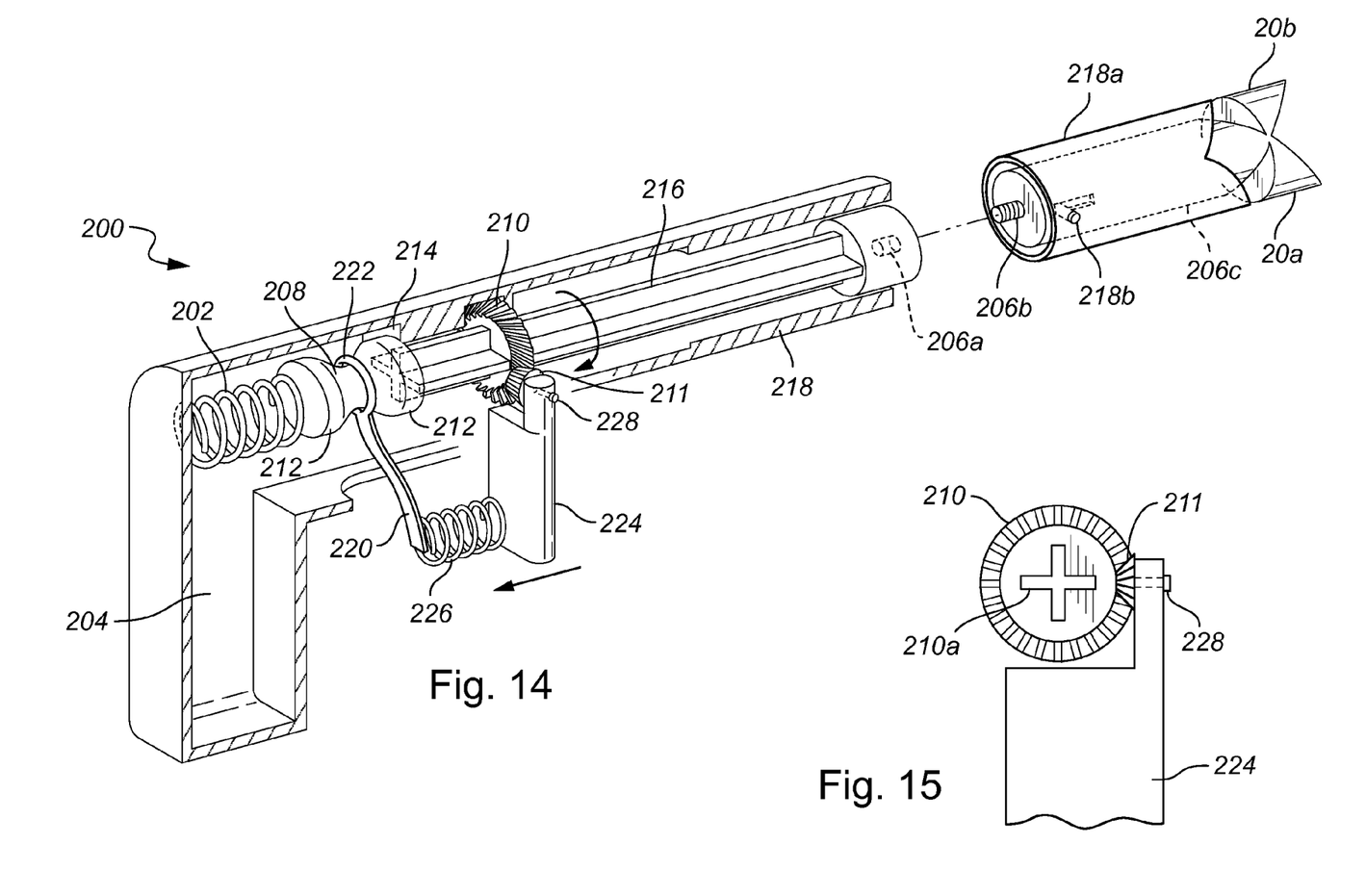
FIG. 14 is a perspective view of an alternative embodiment of scissors.
FIG. 15 is a perspective view of the transmission of the alternative embodiment of scissors.

According to alternative embodiments, different means for rotation can be used to rotate the blades 20a and 20b such as any suitable gear configuration, including perpendicular circular gears, helical gears, rack and pinion gears, spiraled bevel gears, or hyphoid gears. For example, and as shown in FIGS. 14 and 15, an example of handled biopsy scissors 200 is shown. The proximal end of the scissors 200 includes a handle 204 that extends inferiorly from an outer shaft 218 that does not rotate. A trigger or finger grip 224 positioned distally from the handle 204 is coupled at its superior end to a first gear 211 that is configured to operably couple with a second gear 210 operably coupled to an inner shaft 206 such that squeezing the trigger 224 proximally, rotates the first gear 211 which in turn causes the second gear 210 to rotate the inner shaft 206 simultaneously. Further compression of the trigger pulls the inner shaft proximally within the outer shaft 218. As shown in FIG. 15, a non-exclusive example of how the first and second gears 211 and 210 can be operably coupled to one another is provided. More specifically, the inner shaft 206 includes a cross-sectional shape 216 that is configured to be turned by the second gear 210 having a complementary plus-sign cut-out 210a. While a plus-sign cross-sectional shape is shown as 216, additional complementary cross-sectional shapes can work with complementary second gear 210 cut-out shapes so that mechanical rotation and proximal and distal movement of the inner shaft can be accomplished by compressing and releasing the trigger.

With reference to FIG. 14, the distal portion of the inner shaft 206 includes a female connector 206a that is complementary to a male connector 206b on a detachable distal end 206c that functions as a receptacle and includes the blades 20a and 20b. The male and female connectors can be interchanged. Additionally, any suitable type of blades 20a and 20b described above can be used with the handled biopsy scissors 200. The description above relating to the distal and proximal ends 17a and 17b of the inner shaft 17 is also applicable to the detachable distal end 206c and the coupling with the inner shaft 206. While the outer shaft 218 can be continuous (not shown), such that the detachable distal end 206c can be positioned into and out of the distal portion of the outer shaft 218, FIG. 14 depicts a detachable distal end 218a of the outer shaft 218 that is coupled to the inner shaft's detachable distal end 206c by a pin 218b that permits the detachable distal end 206c to slide proximally and distally with respect to the stationary outer shaft's detachable distal end 218a. Preferably, when the inner shaft's detachable distal end 206c is securely coupled to the inner shaft 206, the proximal end of the outer shaft's detachable end 218a abuts with the distal end of the outer shaft 218. This description of a detachable distal end 218a on the outer shaft 218 can also be applicable to the main shaft 1 of the non-handled scissors 100.

With continued reference to FIG. 14, any suitable gear configuration or transmission can be used to cause the inner shaft 206 to rotate and move proximally and distally within the outer shaft 218. The trigger 224 can move proximally and distally by any suitable means, such as a superiorly positioned stationary pin 228 that a superior portion of the trigger 224 can rotate about. Between the trigger 224 and handle 204 is a resilient plate 220 that extends inferiorly from the inner shaft 206. The plate 220 is preferably operably coupled to the trigger 224 through compression means, such as a spring 226. This plate 220 can include or otherwise be operably coupled to a ring 222 positioned superiorly that is configured to fit around a circumferential groove 208 around the proximal end of the inner shaft 206. The plate 220 can be operably coupled to the inner shaft 206 using any suitable means to allow for the inner shaft 206 to slide proximally and distally when the plate 212 respectfully moves proximally and distally. Specifically, when pressure is applied by the blades on the tissue, the trigger 224 is squeezed in a proximal direction and it rotates the inner shaft 206 and blades 20a and 20b, to cut into the tissue. With this initial rotation, the plate 220 remains stationary and is not engaged by the trigger 224. With further proximal compression, the trigger 224 directly or indirectly pushes the plate 220 proximally, which causes the inner shaft 206 to simultaneously slide proximally, thus forcing the closure of the blades 20a and 20b as they make an excision/snipping cut at the base of the targeted tissue. It is preferred the plate 220 is curvilinear as shown in FIG. 14 and resilient such that it can flex proximally and then distally return to its natural position once the compression from the trigger 224 ceases.

Proximal means for compression, such as a spring 202 can be positioned within the superior portion of the handle 204/proximal portion of the outer shaft 218 and operably coupled to the proximal end of the inner shaft 206. When the inner shaft 206 and trigger 224 are in their natural position it is preferred that this spring 202 is slightly compressed. When the proximal compression of the plate 220 causes the inner shaft 206 to proximally slide within the outer shaft 218, the spring 202 is further compressed. As the inner shaft 206 distally returns to its natural position, the spring 202 distally expands, but remains partially compressed. This expansion pushes the inner shaft 206 distally. This distal movement of the inner shaft 206 can be terminated using any suitable stop means. As one example, and as depicted in FIG. 14, the inner shaft 206 and the inside of the outer shaft 218 can include means for stopping the proximal slide of the inner shaft 206. In FIG. 14, the inner shaft 206 includes a protruding circumferential flange 212 that engages with an inwardly protruding rim 214 from the outer shaft 218. The slight compression of the spring 202 is advantageous in pushing the flange 212 into the rim 214 which acts as a stop.

According to further embodiments, the invention can include the blades described herein by themselves or the detachable distal ends of the inner shaft and/or main shaft operably coupled to the blades by themselves. These can be sold as replacement parts or blades and/or can be used to provide users different sizes and/or shapes of blades. Accordingly all description herein directed to blades, inner shafts, mains shafts, releasable attachment, is incorporated into these separate embodiments.

According to preferred embodiments the scissors 100 described herein are sterilized, in their packaging, or otherwise prior to use in collecting tissue samples.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

The invention claimed is:

1. Biopsy scissors comprising:
   a main shaft having distal and proximal ends, external axial threads, and an internal channel traversing proximally and distally;
   an inner shaft traversing proximally and distally within the internal channel of the main shaft, wherein the inner shaft is configured to axially rotate;
   a thumb press positioned at the proximal end of the scissors;
   a winged transmission positioned distally from the thumb press, on the outside of the main shaft, wherein the winged transmission comprises internal axial threads complementary to said axial threads positioned externally on the main shaft, such that when pushing the thumb press, the main shaft is pushed in a distal direction, through the winged transmission, and the complementary axially threaded sections cause the main shaft to rotate forward;
   an internal compression spring positioned within the main shaft between the internal shaft and the thumb press;
   an external compression spring positioned between the thumb press and winged transmission;
   an outer shaft positioned on the outside of the main shaft proximal to the winged transmission and is operably coupled, both rotationally and axially, to the inner shaft; and
   first and second blades individually shaped as semicircles opposite of each other thereby forming a circle together having a given diameter and configured to close towards each other, and open away from each other, at first and second pivot points, wherein the pivot points are positioned opposite of each other at proximal ends of the blades and are coupled to a distal end of the inner shaft, wherein the outside diameter of the proximal end of the first and second blades, in the open position, is substantially equal to the outside diameter of the distal end of the main shaft, and wherein the first and second blades each have a sharp distal facing edge shaped to collectively make a singular circular cut into a targeted site when axially rotated and travelling distally, and wherein the distal end of the main shaft includes first and second external notches positioned opposite of each other and individually aligned proximal to the first and second pivot points of the blades respectively;
   wherein the biopsy scissors are configured such that as the thumb press approaches the winged transmission and the threaded segment of the main shaft passes through the winged transmission, the distal end of the outer shaft collides with the proximal end of the winged transmission forcing the main shaft to move distally over the inner shaft, and the inner shaft to simultaneously move proximally, thereby bringing the first and second pivot points inside the external notches, and colliding with the proximal end of the blades effectuating the first and second blades to close towards each other and simultaneously move proximally by bending at the first and second pivot points.

2. The biopsy scissors of claim 1, wherein the first and second blades are each semicircular blades that are mirror images of each other and individually have concave faces that face towards each other and wherein the distal facing edges are convex.

3. The biopsy scissors of claim 1, wherein the internal shaft comprises a hollowed distal section positioned proximal from and operably coupled to the first and second blades and is configured to receive a cut tissue sample.

4. The biopsy scissors of claim 3, wherein the hollowed distal section of the internal shaft is releasably attachable to a remaining distal section of the internal shaft.

5. The biopsy scissors of claim 3, wherein the internal shaft further comprises a solid section positioned proximally to the hollowed distal section.

6. The biopsy scissors of claim 1, wherein the first and second blades are cut out from a flanged distal end of the inner shaft, which is made of an elastic material, and the first and second pivot points are bend points.

7. The biopsy scissors of claim 1, wherein the first and second blades are coupled to the inner shaft through a pivot point comprising a pin and hole.

8. The biopsy scissors of claim 1, wherein the first and second blades comprise an elastic metal and the pivot points are bend points.

9. The biopsy scissors of claim 1, wherein the main shaft is not configured to collide with the pivot points.

10. A method of collecting a tissue sample from a subject comprising: providing biopsy scissors comprising
  a main shaft having distal and proximal ends, external axial threads, and an internal channel traversing proximally and distally;
  an inner shaft traversing proximally and distally within the internal channel of the main shaft, wherein the inner shaft is configured to axially rotate;
  a thumb press positioned at the proximal end of the scissors;
  a winged transmission positioned distally from the thumb press, on the outside of the main shaft, wherein the winged transmission comprises internal axial threads complementary to said axial threads positioned externally on the main shaft, such that when pushing the thumb press, the main shaft is pushed in a distal direction, through the winged transmission, and the complementary axially threaded sections cause the main shaft to rotate forward;
  an internal compression spring positioned within the main shaft between the internal shaft and the thumb press;
  an external compression spring positioned between the thumb press and winged transmission;
  an outer shaft positioned on the outside of the main shaft proximal to the winged transmission, wherein the outer shaft is operably coupled, both rotationally and axially, to the inner shaft; and
  first and second blades individually shaped as semicircles opposite of each other thereby forming a circle together having a given diameter and configured to close towards each other, and open away from each other, at first and second pivot points, wherein the pivot points are positioned opposite of each other at proximal ends of the blades and are coupled to a distal end of the inner shaft, wherein the outside diameter of the proximal end of the first and second blades, in the open position, is substantially equal to the outside diameter of the distal end of the main shaft, and wherein the first and second blades each have a sharp distal facing edge shaped to collectively make a singular circular cut into a targeted site when axially rotated and travelling distally, and wherein the distal end of the main shaft includes first and second external notches positioned opposite of each other and individually aligned proximal to the first and second pivot points of the blades respectively;
  wherein the biopsy scissors are configured such that as the thumb press approaches the winged transmission and the threaded segment of the main shaft passes through the winged transmission, the distal end of the outer shaft collides with the proximal end of the winged transmission forcing the main shaft to move distally over the inner shaft, and the inner shaft to simultaneously move proximally, thereby bringing the first and second pivot points inside the external notches, and colliding with the proximal end of the blades effectuating the first and second blades to close towards each other and simultaneously move proximally by bending at the first and second pivot points;
  using said biopsy scissors to make a rotational circular cut into the targeted site of the subject and then closing the first and second blades towards each other to excise the tissue sample from the subject.

* * * * *